(12) United States Patent
Bryan et al.

(10) Patent No.: US 6,335,352 B1
(45) Date of Patent: Jan. 1, 2002

(54) IL-8 RECEPTOR ANTAGONISTS

(75) Inventors: Deborah Lynn Bryan, West Chester; John Gerald Gleason, Downington; Katherine L. Widdowson, King of Prussia, all of PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/230,981

(22) PCT Filed: Aug. 15, 1997

(86) PCT No.: PCT/US97/14583

§ 371 Date: Feb. 4, 1999

§ 102(e) Date: Feb. 4, 1999

(87) PCT Pub. No.: WO98/06399

PCT Pub. Date: Feb. 19, 1998

Related U.S. Application Data

(60) Provisional application No. 60/023,988, filed on Aug. 15, 1996.

(51) Int. Cl.$^7$ ............. A61K 31/435; C07D 211/98
(52) U.S. Cl. ............. 514/345; 514/352; 514/357; 546/304; 546/330; 546/329; 546/290; 546/291
(58) Field of Search ............. 546/193, 215, 546/275.1, 276.6, 277.7, 306, 307, 308, 290, 291, 294, 304, 329, 330; 514/227.8, 235.8, 336, 340, 341, 344, 346, 345, 352, 357

(56) References Cited

U.S. PATENT DOCUMENTS

| | | | |
|---|---|---|---|
| 4,057,636 A | * | 11/1977 | Petersen ............. 424/263 |
| 5,262,415 A | | 11/1993 | Takemoto et al. ......... 514/252 |
| 5,371,086 A | | 12/1994 | Takemoto et al. ......... 514/252 |

* cited by examiner

*Primary Examiner*—Alan L. Rotman
*Assistant Examiner*—Rita Desai
(74) *Attorney, Agent, or Firm*—Soma G. Simon; Dara L. Dinner; Charles M. Kinzig

(57) ABSTRACT

Novel compounds useful in the treatment of Interleukin-8 mediated diseases, and methods of using them are disclosed.

6 Claims, No Drawings

IL-8 RECEPTOR ANTAGONISTS

RELATED APPLICATIONS

This application is the §371 national stage entry of PCT/US97/14583, filed Aug. 15, 1997 which claims the benefit of provisional application Ser. No. 60/023,988, filed Aug. 15, 1996.

FIELD OF THE INVENTION

This invention relates to novel guandine substituted compounds, pharmaceutical compositions, processes for their preparation, and use thereof in treating IL-8, GROα, GROβ, GROγ, ENA-78 and NAP-2 mediated diseases.

BACKGROUND OF THE INVENTION

Many different names have been applied to Interleukin-8 (IL-8), such as neutrophil attractant/activation protein-1 (NAP-1), monocyte derived neutrophil chemotactic factor (MDNCF), neutrophil activating factor (NAF), and T-cell lymphocyte chemotactic factor. Interleukin-8 is a chemoattractant for neutrophils, basophils, and a subset of T-cells. It is produced by a majority of nucleated cells including macrophages, fibroblasts, endothelial and epithelial cells exposed to TNF, IL-1α, IL-1β or LPS, and by neutrophils themselves when exposed to LPS or chemotactic factors such as FMLP. M. Baggiolini et al, *J. Clin. Invest.* 84, 1045 (1989); J. Schroder et al, *J. Immunol.* 139, 3474 (1987) and *J. Immunol.* 144, 2223 (1990); Strieter, et al, *Science* 243, 1467 (1989) and *J. Biol. Chem.* 264, 10621 (1989); Cassatella et al, *J. Immunol.* 148, 3216 (1992).

GROα, GROβ, GROγ and NAP-2 also belong to the chemokine α family. Like IL-8 these chemokines have also been referred to by different names. For instance GROα, β, γ have been referred to as MGSAα, β and γ respectively (Melanoma Growth Stimulating Activity), see Richmond et al, *J. Cell Physiology* 129, 375 (1986) and Chang et al, *J. Immunol* 148, 451 (1992). All of the chemokines of the α-family which possess the ELR motif directly preceding the CXC motif bind to the IL-8 B receptor.

IL-8, GROα, GROβ, GROγ and NAP-2 stimulate a number of functions in vitro. They have all been shown to have chemoattractant properties for neutrophils, while IL-8 and GROα have demonstrated T-lymphocytes, and basophiles chemotactic activity. In addition IL-8 can induce histamine release from basophils from both normal and atopic individuals GRO-α and IL-8 can in addition, induce lysozomal enzyme release and respiratory burst from neutrophils. IL-8 has also been shown to increase the surface expression of Mac-1 (CD11b/CD18) on neutrophils without de novo protein synthesis. This may contribute to increased adhesion of the neutrophils to vascular endothelial cells. Many known diseases are characterized by massive neutrophil infiltration. As IL-8, Groα, GROβ, GROγ and NAP-2 promote the accumulation and activation of neutrophils, these chemokines have been implicated in a wide range of acute and chronic inflammatory disorders including psoriasis and rheumatoid arthritis, Baggiolini et al, *FEBS Lett.* 307, 97 (1992); Miller et al, *Crit. Rev. Immunol.* 12, 17 (1992); Oppenheim et al, *Annu. Rev. Immunol.* 9, 617 (1991); Seitz et al., *J. Clin. Invest.* 87, 463 (1991); Miller et al., *Am. Rev. Respir. Dis.* 146, 427 (1992); Donnely et al., *Lancet* 341, 643 (1993). In addition the ELR chemokines (those containing the amino acids ELR motif just prior to the CXC motif) have also been implicated in angiostasis. Strieter et al, *Science* 258, 1798 (1992).

In vitro, IL-8, GROα, GROβ, GROγ and NAP-2 induce neutrophil shape change, chemotaxis, granule release, and respiratory burst, by binding to and activating receptors of the seven-transmembrane, G-protein-linked family, in particular by binding to IL-8 receptors, most notably the B-receptor. Thomas et al., *J. Biol. Chem.* 266, 14839 (1991); and Holmes et al., *Science* 253, 1278 (1991). The development of non-peptide small molecule antagonists for members of this receptor family has precedent. For a review see R. Freidinger in: *Progress in Drug Research*, Vol. 40, pp. 33–98, Birkhauser Verlag, Basel 1993. Hence, the IL-8 receptor represents a promising target for the development of novel anti-inflammatory agents.

Two high affinity human IL-8 receptors (77% homology) have been characterized: IL-8Rα, which binds only IL-8 with high affinity, and IL-8Rβ, which has high affinity for IL-8 as well as for GRO-α, GROβ, GROγ and NAP-2. See Holmes et al., supra; Murphy et al., *Science* 253, 1280 (1991); Lee et al.,*J. Biol. Chem.* 267, 16283 (1992); LaRosa et al., *J. Biol. Chem.* 267, 25402 (1992); and Gayle et al.,*J. Biol. Chem.* 268, 7283 (1993).

There remains a need for treatment, in this field, for compounds which are capable of binding to the IL-8 α or β receptor. Therefore, conditions associated with an increase in IL-8 production (which is responsible for chemotaxis of neutrophil and T-cells subsets into the inflammatory site) would benefit by compounds which are inhibitors of IL-8 receptor binding.

SUMMARY OF THE INVENTION

This invention provides for a method of treating a chemokine mediated disease, wherein the chemokine is one which binds to an IL-8 α or β receptor and which method comprises administering an effective amount of a compound of Formula (I) or a pharmaceutically acceptable salt thereof. In particular the chemokine is IL-8.

This invention also relates to a method of inhibiting the binding of IL-8 to its receptors in a mammal in need thereof which comprises administering to said mammal an effective amount of a compound of Formula (I).

Compounds of Formula (I) useful in the present invention are represented by the structure:

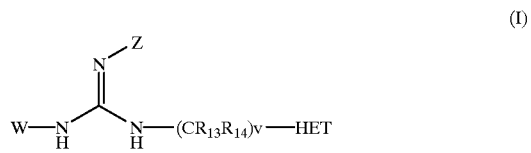

wherein

Z is cyano, $OR_{11}$, $C(O)NR_{15}R_{16}$, $R_{18}$, $C(O)OR_{11}$, $C(O)R_{11}$, or $S(O)_2R_{17}$;

R is any functional moiety having an ionizable hydrogen and a pKa of 10 or less;

$R_1$ is independently selected from hydrogen; halogen; nitro; cyano; halosubstituted $C_{1-10}$ alkyl; $C_{1-10}$ alkyl; $C_{2-10}$ alkenyl; $C_{1-10}$ alkoxy; halosubstituted $C_{1-10}$ alkoxy; azide; $(CR_8R_8)qS(O)_tR_4$; hydroxy; hydroxy $C_{1-4}$alkyl; aryl; aryl $C_{1-4}$ alkyl; aryloxy; aryl $C_{1-4}$ alkyloxy; heteroaryl; heteroarylalkyl; heterocyclic, heterocyclic $C_{1-4}$alkyl; heteroaryl $C_{1-4}$ alkyloxy; aryl $C_{2-10}$ alkenyl; heteroaryl $C_{2-10}$ alkenyl; heterocyclic $C_{2-10}$ alkenyl; $(CR_8R_8)qNR_4R_5$; $C_{2-10}$ alkenyl $C(O)$ $NR_4R_5$; $(CR_8R_8)qC(O)NR_4R_5$; $(CR_8R_8)qC(O)$ $NR_4R_{10}$; $S(O)_3H$; $S(O)_3R_8$; $(CR_8R_8)qC(O)R_{11}$; $C_{2-10}$ alkenyl $C(O)R_{11}$; $C_{2-10}$ alkenyl $C(O)OR_{11}$; $(CR_8R_8)qC(O)OR_{12}$; $(CR_8R_8)qOC(O)R_{11}$; $(CR_8R_8)qNR_4C(O)R_{11}$; $(CR_8R_8)qNHS(O)_2R_{19}$; $(CR_8R_8)_qS(O)_2NR_4R_5$; or two $R_1$ moieties together may form O—$(CH_2)_s$O— or a 5 to 6 membered saturated or unsaturated ring, and wherein the aryl, heteroaryl and heterocyclic containing moieties may be optionally substituted;

q is 0, or an integer having a value of 1 to 10;

t is 0, or an integer having a value of 1 or 2;

m is an integer having a value of 1 to 3;

s is an integer having a value of 1 to 3;

$R_4$ and $R_5$ are independently hydrogen, optionally substituted $C_{1-4}$ alkyl, optionally substituted aryl, optionally substituted aryl $C_{1-4}$alkyl, optionally substituted heteroaryl, optionally substituted heteroaryl $C_{1-4}$alkyl, heterocyclic, or heterocyclic $C_{1-4}$ alkyl, or $R_4$ and $R_5$ together with the nitrogen to which they are attached form a 5 to 7 member ring which may optionally comprise an additional heteroatom selected from oxygen, nitrogen or sulfur;

HET is an optionally substituted heteroaryl moiety;

$R_6$ and $R_7$ are independently hydrogen or a $C_{1-4}$ alkyl group; or $R_6$ and $R_7$ together with the nitrogen to which they are attached form a 5 to 7 member ring which ring may optionally contain an additional heteroatom selected from oxygen, nitrogen or sulfur;

$R_8$ is independently selected from hydrogen or $C_{1-4}$ alkyl;

$R_{10}$ is $C_{1-10}$ alkyl $C(O)_2R_8$ $R_{11}$ is hydrogen, $C_{1-4}$ alkyl, optionally substituted aryl, optionally substituted aryl $C_{1-4}$alkyl, optionally substituted heteroaryl, optionally substituted heteroaryl$C_{1-4}$alkyl, optionally substituted heterocyclic, or optionally substituted heterocyclic$C_{1-4}$alkyl;

$R_{12}$ is hydrogen, $C_{1-10}$ alkyl, optionally substituted aryl or optionally substituted arylalkyl;

$R_{13}$ and $R_{14}$ are independently hydrogen or $C_{1-4}$ alkyl;

v is 0, or an integer having a value of 1 to 4;

$R_{15}$ and $R_{16}$ are independently hydrogen, optionally substituted $C_{1-4}$ alkyl, optionally substituted aryl, optionally substituted aryl $C_{1-4}$alkyl, optionally substituted heteroaryl, optionally substituted heteroaryl$C_{1-4}$alkyl, optionally substituted heterocyclic, optionally substituted heterocyclic$C_{1-4}$alkyl, or $R_{15}$ and $R_{16}$ may together with the nitrogen to which they are attached form a 5 to 7 member ring optionally containing an additional heteroatom selected from oxygen, nitrogen, or sulfur;

$R_{17}$ is $C_{1-4}$ alkyl, $NR_{15}R_{16}$, $OR_{11}$, optionally substituted aryl, optionally substituted aryl $C_{1-4}$alkyl, optionally substituted heteroaryl, optionally substituted heteroaryl$C_{1-4}$alkyl, optionally substituted heterocyclic, or optionally substituted heterocyclic$C_{1-4}$alkyl;

$R_{18}$ is optionally substituted $C_{1-4}$ alkyl, optionally substituted aryl, optionally substituted aryl $C_{1-4}$alkyl, optionally substituted heteroaryl, optionally substituted heteroaryl$C_{1-4}$alkyl, optionally substituted heterocyclic, or optionally substituted heterocyclic$C_{1-4}$alkyl;

$R_{19}$ is $C_{1-4}$alkyl, aryl, arylalkyl, heteroaryl, heteroaryl$C_{1-4}$alkyl, heterocyclic, or heterocyclic$C_{1-4}$alkyl, wherein the all of these moieties may be optionally substituted;

$R_d$ is $NR_6R_7$, alkyl, aryl$C_{1-4}$ alkyl, aryl$C_{2-4}$ alkenyl, heteroaryl, hetroaryl-$C_{1-4}$alkyl, heteroaryl$C_{2-4}$ alkenyl, heterocyclic, heterocyclic$C_{1-4}$ alkyl, wherein the alkyl, aryl, arylalkyl, heteroaryl, heteroaryl alkyl, heterocyclic, and heterocyclic alkyl rings may be optionally substituted;

W is 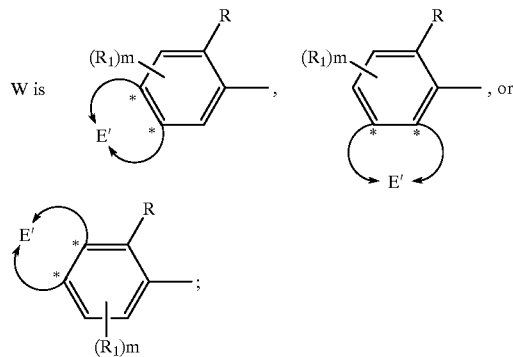

the E' containing ring is optionally selected from

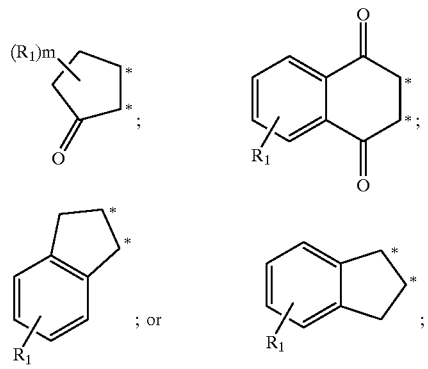

the asterix * denoting point of attachment of the ring; or a pharmaceutically acceptable salt thereof.

DETAILED DESCRIPTION OF THE INVENTION

The compounds of Formula (I) may also be used in association with the veterinary treatment of mammals, other than humans, in need of inhibition of IL-8 or other chemokines which bind to the IL-8 α and β receptors. Chemokine mediated diseases for treatment, therapeutically or prophylactically, in animals include disease states such as those noted herein in the Methods of Treatment section.

In compounds of Formula (I), W is suitably

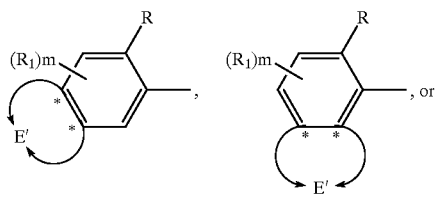

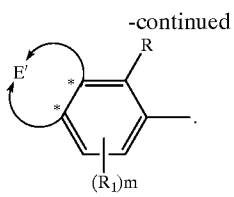
-continued

The E' containing ring, denoted by its point of attachment through the asterix (*) may optionally be present. If if it is not present the ring is a phenyl moiety which is substituted by the $R_1$ terms as shown. The E' ring may be substituted by the $R_1$ moiety in any ring, saturated or unsaturated, and is shown for purposes herein substituted only in the unsaturated ring(s).

R is suitably any functional moiety which provides an ionizable hydrogen having a pKa of 10 or less, preferably from about 3 to 9, more preferably from about 3 to 7. Such functional groups include, but are not limited to, hydroxy, carboxylic acid, thiol, $SR_2$, $OR_2$, NH—$C(O)R_a$, $C(O)NR_6R_7$, a substituted sulfonamides of the formula: $NHS(O)_2R_b$, $S(O)_2NHR_c$, $NHC(X_2)NHR_b$, or a tetrazolyl; wherein $X_2$ is oxygen or sulfur, preferably oxygen. Preferably, the functional group is other than a sulfonic acid, either directly or as a substituent group on the aryl, heteroaryl, or heterocyclic moiety ring, such as in $SR_2$ or $OR_2$. More preferably R is OH, SH, or $NHS(O)_2R_b$.

Suitably, $R_2$ is a substituted aryl, heteroaryl, or heterocyclic moiety which ring has the functional moiety providing the ionizable hydrogen having a pKa of 10 or less.

Suitably, $R_{6'}$ and $R_{7'}$ are hydrogen, $C_{1-4}$ alkyl, aryl, aryl$C_{1-4}$alkyl, aryl$C_{2-4}$alkenyl, heteroaryl, heteroaryl $C_{1-4}$alkyl, heteroaryl$C_{2-4}$ alkenyl, heterocyclic, heterocyclic $C_{1-4}$alkyl, heterocyclic $C_{2-4}$alkenyl moiety, all of which may be optionally substituted one to three times independently by halogen; nitro; halosubstituted $C_{1-4}$ alkyl, such as $CF_3$; $C_{1-4}$ alkyl, such as methyl; $C_{1-4}$ alkoxy, such as methoxy; $NR_9C(O)R_a$; $C(O)NR_6R_7$; $S(O)_3H$; or $C(O)OC_{1-4}$ alkyl, provided that only one of $R_{6'}$ and $R_{7'}$ are hydrogen, but not both.

Suitably, $R_6$ and $R_7$ are independently hydrogen or a $C_{1-4}$ alkyl group, or $R_6$ and $R_7$ together with the nitrogen to which they are attached form a 5 to 7 member ring which ring may optionally contain an additional heteroatom which heteroatom is selected from oxygen, nitrogen or sulfur. This heteroring may be optionally substituted as defined herein.

Suitably $R_a$ is an aryl, aryl$C_{1-4}$alkyl, heteroaryl, heteroaryl$C_{1-4}$alkyl, heterocyclic, or a heterocyclic $C_{1-4}$alkyl moiety, all of which may be optionally substituted, as defined herein below.

Suitably, $R_b$ is a $NR_6R_7$, alkyl, aryl, aryl$C_{1-4}$alkyl, aryl $C_{2-4}$alkenyl, heteroaryl, heteroaryl$C_{1-4}$alkyl, heteroaryl$C_{2-4}$ alkenyl, heterocyclic, heterocyclic $C_{1-4}$alkyl, heterocyclic $C_{2-4}$alkenyl moiety, or camphor, all of which may be optionally substituted one to three times independently by halogen; nitro; halosubstituted $C_{1-4}$ alkyl, such as $CF_3$; $C_{1-4}$ alkyl, such as methyl; $C_{1-4}$ alkoxy, such as methoxy; $NR_9C(O)R_a$; $C(O)NR_6R_7$; $S(O)_3H$; or $C(O)OC_{1-4}$ alkyl. $R_b$ is preferably an optionally substituted phenyl, benzyl, or styryl. When $R_b$ is a heteroaryl preferably it is an optionally substituted thiazole, optionally substituted thienyl, or optionally substituted quinolinyl ring.

Suitably $R_9$ is hydrogen or a $C_{1-4}$ alkyl, preferably hydrogen. Preferably, when the substituent group is $NR_9C(O)R_a$, then $R_a$ is preferably an alkyl group, such as methyl.

Suitably $R_c$ is hydrogen, alkyl, aryl, aryl$C_{1-4}$alkyl, aryl $_{1-4}$alkenyl, heteroaryl, heteroaryl$C_{1-4}$alkyl, heteroaryl $C_{1-4}$alkenyl, heterocyclic, heterocyclic $C_{1-4}$alkyl, or heterocyclic $C_{1-4}$alkenyl moiety, all of which may be optionally substituted one to three times independently by halogen, nitro, halosubstituted $C_{1-4}$ alkyl, $C_{1-4}$ alkyl, $C_{1-4}$ alkoxy, $NR_9C(O)R_a$, $C(O)NR_6R_7$, $S(O)_3H$, or $C(O)OC_{1-4}$ alkyl. Preferably, $R_c$ is an optionally substituted phenyl.

When R is an $OR_2$ or $SR_2$ moiety it is recognized by one of skill in the art that the aryl ring must, therefore, contain the required ionizable hydrogen. The aryl ring may also be additionally substituted, independently, by one to three groups, which groups may also contain an additional ionizable group, and which include but are not limited to, halogen, nitro, halosubstituted $C_{1-4}$ alkyl, $C_{1-4}$ alkyl, $C_{1-4}$ alkoxy, hydroxy, SH, $C(O)NR_6R_7$, NH—$C(O)R_a$, NH $S(O)_2R_b$, $S(O)_2NR_6R_7$, $C(O)OR_8$, or a tetrazolyl ring.

In compounds of Formula (I), suitably $R_1$ is independently selected from hydrogen; halogen; nitro; cyano; halosubstituted $C_{1-10}$ alkyl, such as $CF_3$; $C_{1-10}$ alkyl, such as methyl, ethyl, isopropyl, or n-propyl; $C_{2-10}$ alkenyl; $C_{1-10}$ alkoxy, such as methoxy, or ethoxy; halosubstituted $C_{1-10}$ alkoxy, such as trifluoromethoxy; azide; $(CR_8R_8)q$ $S(O)_tR_4$, wherein t is 0, 1 or 2; hydroxy; hydroxy $C_{1-4}$alkyl, such as methanol or ethanol; aryl, such as phenyl or naphthyl; aryl $C_{1-4}$ alkyl, such as benzyl; aryloxy, such as phenoxy; aryl $C_{1-4}$ alkyloxy, such as benzyloxy; heteroaryl; heteroarylalkyl; heteroaryl $C_{1-4}$ alkyloxy; aryl $C_{2-10}$ alkenyl; heteroaryl $C_{2-10}$ alkenyl; heterocyclic $C_{2-10}$ alkenyl; $(CR_8R_8)qNR_4R_5$; $C_{2-10}$ alkenyl $C(O)NR_4R_5$; $(CR_8R_8)q$ $C(O)NR_4R_5$; $(CR_8R_8)q$ $C(O)NR_4R_{10}$; $S(O)_3H$; $S(O)_3R_8$; $(CR_8R_8)q$ $C(O)$ $R_{11}$; $C_{2-10}$ alkenyl $C(O)R_{11}$; $C_{2-10}$ alkenyl $C(O)OR_{11}$; $C(O)$ $R_{11}$; $(CR_8R_8)q$ $C(O)OR_{12}$; $(CR_8R_8)qOC(O)R_{11}$; $(CR_8R_8)q$ $NR_4C(O)R_{11}$; $(CR_8R_8)q$ $NHS(O)_2R_{19}$; or $(CR_8R_8)q$ $S(O)_2NR_4R_5$; or two $R_1$ moieties together may form O—$(CH_2)_sO$— or a 5 to 6 membered saturated or unsaturated ring: and s is an integer having a value of 1 to 3. The aryl, heteroaryl, and heterocyclic containing moieites may be optionally substituted as defined herein below.

Suitably, q is 0, or an integer having a value of 1 to 10.

When $R_1$ forms a dioxybridge, s is preferably 1. When $R_1$ forms an additional saturated or unsaturated ring, it is preferably 6 membered ring resulting in a naphthylene ring system. These rings may be substituted independently, 1 to 3 times by the other $R_1$ moieties as defined above.

Suitably, $R_4$ and $R_5$ are independently hydrogen, optionally substituted $C_{1-4}$ alkyl, optionally substituted aryl, optionally substituted aryl $C_{1-4}$alkyl, optionally substituted heteroaryl, optionally substituted heteroaryl $C_{1-4}$alkyl, heterocyclic, heterocyclic$C_{1-4}$ alkyl, or $R_4$ and $R_5$ together with the nitrogen to which they are attached form a 5 to 7 member ring which may optionally comprise an additional heteroatom selected from O/N/S.

$R_8$ is suitably independently selected from hydrogen or $C_{1-4}$ alkyl.

$R_{10}$ is suitably $C_{1-10}$ alkyl $C(O)_2R_8$, such as $CH_2C(O)_2H$ or $CH_2C(O)_2CH_3$.

$R_{11}$ is suitably hydrogen, $C_{1-4}$ alkyl, aryl, aryl $C_{1-4}$ alkyl, heteroaryl, heteroaryl $C_{1-4}$alkyl, heterocyclic, or heterocyclic $C_{1-4}$alkyl.

$R_{12}$ is suitably hydrogen, $C_{1-10}$ alkyl, optionally substituted aryl or optionally substituted arylalkyl.

$R_{19}$ is $C_{1-4}$alkyl, aryl, arylalkyl, heteroaryl, heteroaryl$C_{1-4}$alkyl, heterocyclic, or heterocyclic$C_{1-4}$alkyl, wherein the all of these moieties may be optionally substituted;

Preferably $R_1$ is halogen, cyano, nitro, $CF_3$, $C(O)NR_4R_5$, alkenyl $C(O)NR_4R_5$, $C(O)$ $R_4R_{10}$, alkenyl $C(O)OR_{12}$, heteroaryl, heteroarylalkyl, heteroaryl alkenyl, or S(O)NR$_4$R$_5$, and preferably R$_4$ and R$_5$ are both hydrogen or one is phenyl. A preferred ring substitution for R$_1$ is in the 4-position of the phenyl ring.

When R is OH, SH or NS$_2$R$_b$, than R$_1$ is preferably mono-substituted in the 3-position, the 4-position or is di substituted in the 3,4-position. The substituent group is suitably an electron withdrawing moiety. Preferably when R is OH, SH or NSO$_2$R$_b$, than R$_1$ is nitro, halogen, cyano, trifluoromethyl group, C(O)NR$_4$R$_5$.

When R is carboxylic acid, than R$_1$ is preferably hydrogen, or R$_1$ is preferably substituted in the 4-position, more preferably substituted by trifluoromethyl or chloro.

In compounds of Formula (I), suitably R$_{13}$ and R$_{14}$ are independently hydrogen, optionally substituted C$_{1-4}$ alkyl which may be straight or branched as defined herein, or one of R$_{13}$ and R$_{14}$ are an optionally substituted aryl; v is 0, or an integer having a value of 1 to 4.

When R$_{13}$ or R$_{14}$ are an optionally substituted alkyl, the alkyl moiety may be substituted one to three times independently by halogen; halosubstituted C$_{1-4}$ alkyl such as trifluromethyl; hydroxy; hydroxy C$_{1-4}$alkyl, C$_{1-4}$ alkoxy; such as methoxy, or ethoxy, halosubstituted C$_{1-10}$ alkoxy, S(O)$_r$R$_4$; aryl; NR$_4$R$_5$; NHC(O)R$_4$; C(O)NR$_4$R$_5$; or C(O)OR$_8$.

In compounds of Formula (I), Z is suitably cyano, OR$_{11}$, C(O)NR$_{15}$R$_{16}$, R$_{18}$, C(O)R$_{11}$, C(O)OR$_{11}$, or S(O)$_2$R$_{17}$.

Suitably R$_{15}$ and R$_{16}$ are independently hydrogen, optionally substituted C$_{1-4}$ alkyl, optionally substituted aryl, optionally substituted aryl C$_{1-4}$alkyl, optionally substituted heteroaryl, optionally substituted heteroarylC$_{1-4}$alkyl, optionally substituted heterocyclic, optionally substituted heterocyclicC$_{1-4}$alkyl, or R$_{15}$ and R$_{16}$ may together with the nitrogen to which they are attached form a 5 to 7 member ring optionally containing an additional heteroatom selected from oxygen, nitrogen, or sulfur.

Suitably, R$_{17}$ is C$_{1-4}$ alkyl, NR$_{15}$R$_{16}$, OR$_{11}$, optionally substituted aryl, optionally substituted aryl C$_{1-4}$alkyl, optionally substituted heteroaryl, optionally substituted heteroarylC$_{1-4}$alkyl, optionally substituted heterocyclic, or optionally substituted heterocyclicC$_{1-4}$alkyl.

In compounds of Formula (I), R$_{18}$ is suitably hydrogen, halogen, cyano, optionally substituted C$_{1-4}$ alkyl, halo substituted C$_{1-4}$ alkyl, C(O)NR$_{15}$R$_{16}$, optionally substituted aryl, optionally substituted aryl C$_{1-4}$alkyl, optionally substituted heteroaryl, optionally substituted heteroarylC$_{1-4}$alkyl, optionally substituted heterocyclic, or optionally substituted heterocyclicC$_{1-4}$alkyl.

In compounds of Formula (I), HET is suitably a heteroaryl ring or multi-ring system. If the HET moiety is a multi ring system, the ring containing the heteroatom does not need to be directly attached to the urea moiety. All the rings in this ring system may be optionally substituted as defined herein. Preferably the HET moiety is a pyridyl, which may be 2-, 3- or 4-pyridyl. If the ring is a multi system ring it is preferably benzimidazole, dibenzothiophene, or an indole ring. Other heterocyclic rings of interest include, but are not limited to thiophene, furan, pyrimidine, pyrrole, pyrazole, quinoline, isoquinoline, quinazolinyl, pyridine, oxazole, thiazole, thiadiazole, triazole, imidazole, or benzimidazole.

In compounds of Formula (I), the HET ring may be optionally substituted independently one to three times by Y, i.e. (Y$_{(n)}$), wherein n is an integer having a value of 1 to 3. Suitably, Y is independently selected from hydrogen; halogen; nitro; cyano; halosubstituted C$_{1-10}$ alkyl; C$_{1-10}$ alkyl; C$_{2-10}$ alkenyl; C$_{1-10}$ alkoxy; halosubstituted C$_{1-10}$ alkoxy; azide; (CR$_8$R$_8$)q S(O)$_t$R$_4$; hydroxy; hydroxyC$_{1-4}$alkyl; aryl; aryl C$_{1-4}$ alkyl; aryloxy; arylC$_{1-4}$ alkyloxy; heteroaryl; heteroarylalkyl; heteroaryl C$_{1-4}$ alkyloxy; heterocyclic, heterocyclic C$_{1-4}$alkyl; aryl C$_{2-10}$ alkenyl; heteroaryl C$_{2-10}$ alkenyl; heterocyclic C$_{2-10}$ alkenyl; (CR$_8$R$_8$)q NR$_4$R$_5$; C$_{2-10}$ alkenyl C(O)NR$_4$R$_5$; (CR$_8$R$_8$)q C(O)NR$_4$R$_5$; (CR$_8$R$_8$)$_q$ C(O)NR$_4$R$_{10}$; S(O)$_3$H; S(O)$_3$R$_8$; (CR$_8$R$_8$)q C(O)R$_{11}$; C$_{2-10}$ alkenyl C(O)R$_{11}$; C$_{2-10}$ alkenyl C(O)OR$_{11}$; (CR$_8$R$_8$)q C(O)OR$_{12}$; (CR$_8$R$_8$)q OC(O)R$_{11}$; (CR$_8$R$_8$)q NR$_4$C(O)R$_{11}$; (CR$_8$R$_8$)q NHS(O)$_2$R$_d$; (CR$_8$R$_8$)q S(O)$_2$NR$_4$R$_5$; or two Y moieties together may form O—(CH$_2$)$_s$O— or a 5 to 6 membered saturated or unsaturated ring; wherein the aryl, heteroaryl, heterocyclic containing moieties may be optionally substituted as defined herein.

When Y forms a dioxybridge, s is preferably 1. When Y forms an additional saturated or unsaturated ring, it is preferably 6 membered ring resulting in a naphthylene ring system. These rings may also be substituted 1 to 3 times by other Y moieties as defined above.

Suitably, R$_d$ is a NR$_6$R$_7$, alkyl, aryl C$_{1-4}$ alklyl, arylC$_{2-4}$ alkenyl, heteroaryl, hetroaryl-C$_{1-4}$alkyl, heteroarylC$_{2-4}$ alkenyl, heterocyclic, heterocyclicC$_{1-4}$ alkyl, or heterocyclic C$_{2-4}$ alkenyl moiety, wherein the aryl, heteroaryl, and heterocyclic containing moieties may all be optionally substituted as defined herein.

As used herein, "optionally substituted" unless specifically defined shall mean such groups as halogen, such as fluorine, chlorine, bromine or iodine; hydroxy; hydroxy substituted C$_{1-10}$alkyl; C$_{1-10}$ alkoxy, such as methoxy or ethoxy; S(O)$_{m'}$ C$_{1-10}$ alkyl, wherein m' is 0, 1 or 2, such as methyl thio, methyl sulfinyl or methyl sulfonyl; amino, mono & di-substituted amino, such as in the NR$_4$R$_5$ group; NHC(O)R$_4$; C(O)NR$_4$R$_5$; C(O)OH; S(O)$_2$NR$_4$R$_5$; NH S(O)$_2$R$_{21}$, C$_{1-10}$ alkyl, such as methyl, ethyl, propyl, isopropyl, or t-butyl; halosubstituted C$_{1-10}$ alkyl, such CF$_3$; an optionally substituted aryl, such as phenyl, or an optionally substituted arylalkyl, such as benzyl or phenethyl, optionally substituted heterocylic, optionally substituted heterocylicalkyl, optionally substituted heteroaryl, optionally substituted heteroaryl alkyl, wherein these aryl, hetroaryl, or heterocyclic moieties may be substituted one to two times by halogen; hydroxy; hydroxy substituted alkyl; C$_{1-10}$ alkoxy; S(O)$_{m'}$C$_{1-10}$ alkyl; amino, mono & di-substituted amino, such as in the NR$_4$R$_5$ group; C$_{1-10}$ alkyl, or halosubstituted C$_{1-10}$ alkyl, such as CF$_3$.

R$_{21}$ is suitably C$_{1-4}$ alkyl, aryl, aryl C$_{1-4}$alkyl, heteroaryl, heteroarylC$_{1-4}$alkyl, heterocyclic, or heterocyclicC$_{1-4}$alkyl.

Suitable pharmaceutically acceptable salts are well known to those skilled in the art and include basic salts of inorganic and organic acids, such as hydrochloric acid, hydrobromic acid, sulphuric acid, phosphoric acid, methane sulphonic acid, ethane sulphonic acid, acetic acid, malic acid, tartaric acid, citric acid, lactic acid, oxalic acid, succinic acid, fumaric acid, maleic acid, benzoic acid, salicylic acid, phenylacetic acid and mandelic acid. In addition, pharmaceutically acceptable salts of compounds of Formula (I) may also be formed with a pharmaceutically acceptable cation, for instance, if a substituent group comprises a carboxy moiety. Suitable pharmaceutically acceptable cations are well known to those skilled in the art and include alkaline, alkaline earth, ammonium and quaternary ammonium cations.

The following terms, as used herein, refer to:

"halo"—all halogens, that is chloro, fluoro, bromo and iodo.

"C$_{1-10}$alkyl" or "alkyl"—both straight and branched chain radicals of 1 to 10 carbon atoms, unless the chain length is otherwise limited, including, but not limited to, methyl, ethyl, n-propyl, iso-propyl, n-butyl, sec-butyl, iso-butyl, tert-butyl, n-pentyl and the like.

The term "cycloalkyl" is used herein to mean cyclic radicals, preferably of 3 to 8 carbons, including but not limited to cyclopropyl, cyclopentyl, cyclohexyl, and the like.

The term "alkenyl" is used herein at all occurrences to mean straight or branched chain radical of 2–10 carbon atoms, unless the chain length is limited thereto, including, but not limited to ethenyl, 1-propenyl, 2-propenyl, 2-methyl-1-propenyl, 1-butenyl, 2-butenyl and the like.

"aryl"—phenyl and naphthyl;

"heteroaryl" (on its own or in any combination, such as "heteroaryloxy", or "heteroaryl alkyl")—a 5–10 membered aromatic ring system in which one or more rings contain one or more heteroatoms selected from the group consisting of N, O or S, such as, but not limited, to pyrrole, pyrazole, furan, thiophene, quinoline, isoquinoline, quinazolinyl, pyridine, pyrimidine, oxazole, thiazole, thiadiazole, triazole, imidazole, or benzimidazole.

"heterocyclic" (on its own or in any combination, such as "heterocyclicalkyl")—a saturated or partially unsaturated 4–10 membered ring system in which one or more rings contain one or more heteroatoms selected from the group consisting of N, O, or S; such as, but not limited to, pyrrolidine, piperidine, piperazine, morpholine, tetrahydropyran, or imidazolidine.

The term "arylalkyl" or "heteroarylalkyl" or "heterocyclicalkyl" is used herein to mean $C_{1-10}$ alkyl, as defined above, attached to an aryl, heteroaryl or heterocyclic moiety, as also defined herein, unless otherwise indicated.

"sulfinyl"—the oxide S (O) of the corresponding sulfide, the term "thio" refers to the sulfide, and the term "sulfonyl" refers to the fully oxidized $S(O)_2$ moiety.

The term "wherein two $R_1$ moieties (or two Y moieties) may together form a 5 or 6 membered saturated or unsaturated ring" is used herein to mean the formation of a napthylene ring system or a phenyl moiety having attached a 6 membered partially unsaturated ring such as a $C_6$ cycloalkenyl, i.e hexene, or a $C_5$ cyloalkenyl moiety, cyclopentene.

It is recognized that the compounds of the present invention may exist as stereoisomers, regioisomers, or diastereiomers. These compounds may contain one or more asymmetric carbon atoms and may exist in racemic and optically active forms. All of these compounds are included within the scope of the present invention.

The compounds of Formula (I) may be obtained by applying synthetic procedures, some of which are illustrated in the Schemes below. The synthesis provided for in these Schemes is applicable for the producing compounds of Formula (I) having a variety of different R, $R_1$, and Aryl groups which are reacted, employing optional substituents which are suitably protected, to achieve compatibility with the reactions outlined herein. Subsequent deprotection, in those cases, then affords compounds of the nature generally disclosed. Once the urea nucleus has been established, further compounds of these formulas may be prepared by applying standard techniques for functional group interconversion, well known in the art. While the schemes are shown with compounds only of Formula (I) this is merely for illustration purposes only.

Methods of Preparation

The title compounds can be synthesized from the thiouronium salt (2, Scheme 1). R' represents the $(R_{13}R_{14})_v$-HET linkage as defined in compounds of Formula (I). Z is also as defined in compounds of Formula (I). For purposes of illustration herein the schemes represent the W term by a substituted phenyl.

Scheme 1

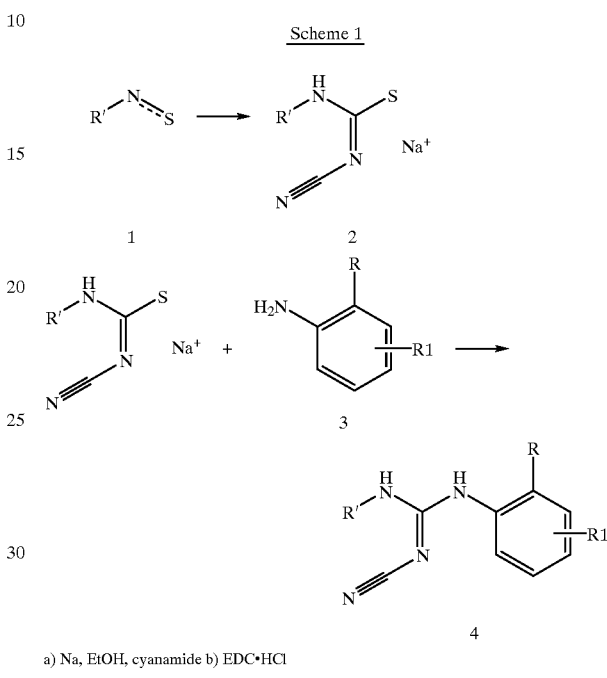

a) Na, EtOH, cyanamide b) EDC·HCl

The thiouronium salt(2, Scheme 1) can be synthesized by reacting sodium cyanamide with a commercially available isothiocyanate 1 (if the isothiocyanate is not commercially available it can be synthesized by reacting the desired amine with thiophosgene in the presence of a base like sodium bicarbonate). The thiouronium salt (2) can then be condensed with the appropriate substituted aniline in the presence of a coupling reagent like EDC.HCl or acidified to form the cyanothiourea and then reacted.

Alternatively 4 can be synthesized by reacting the commercially available (Aldrich Chem. Co.), diphenyl cyanocarboimidate (5, Scheme 2) with an amine to form an intermediate O-phenylisourea 6 which then reacts with the appropriately substituted aniline in the presence of trimethyl aluminum by the method of Atwal. (Atwal, K. S., Tetrahedron Lett, 35, 8085 (1994).). Compounds wherein R' is alkyl may be prepared by heating with the appropriately substituted alkylamine, but without the presence of catalyst.

Scheme 2

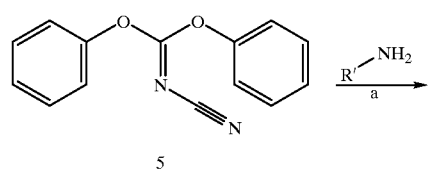

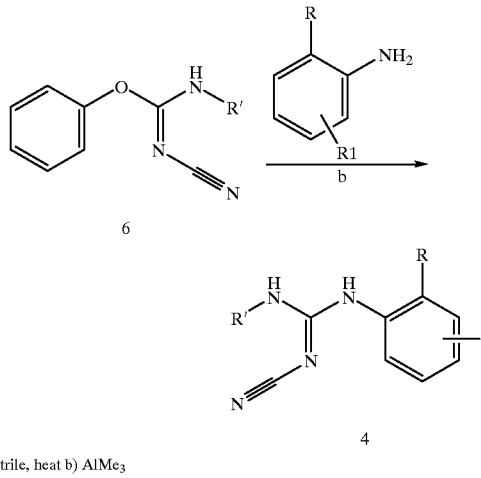

a) acetonitrile, heat b) AlMe₃

Alternatively the title compound can be synthesized using a protected ortho-substituted aniline (8, Scheme 3, See synthesis as described in U.S. provisional application U.S. Ser. No. 60/020655 filed Jun. 27, 1996, WO96/25157 filed Aug. 22, 1996, Widdowson et al.; and U.S. Ser. No. 08/701,299 filed Aug. 22, 1996 whose disclosures are incorporated herein by reference in their entirety. An ortho-substituted aniline (7, Scheme 3) is first protected (ie. tert-butyl dimethyl silyl, allyl, benzyl, mom or other suitable protecting group) by reacting the ortho-substituted aniline with the appropriate alkyl or silyl halide in the presence of a suitable base (ie. cesium carbonate, potassium carbonate or imidazole) in an aprotic solvent. The protected ortho-substituted aniline may also be synthesized from an ortho-substituted nitrobenzene (9) by reacting it with a protecting group under conditions well known in the art (see Greene, T *Protecting Groups in Organic Synthesis,* Wiley & Sons, New York, 1981) This protected ortho-substituted nitro compound is then reduced to the corresponding aniline using SnCl₂ in EtOH or alternately H₂/Pd or LiAlH₄ in an aprotic solvent.

Scheme 3

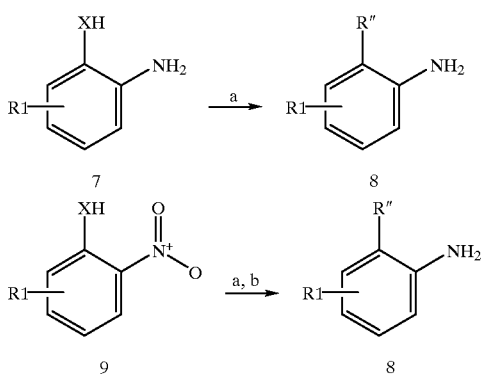

X = N, O, S a) Alkyl or silyl halide, base b) reducing agent

This protected ortho-substituted aniline (8) can then be converted into an isothiocyanate using thiophosgene and then reacted with the anion ZNH⁻ (formed from reaction of ZNH₂ with a base such as NaH). Z is as defined in compounds of Formula (I). The resulting thioanion can then be alkylated with an alkylating agent like methyl iodide to form a thioimidate such as 10 (Scheme 4).

Scheme 4

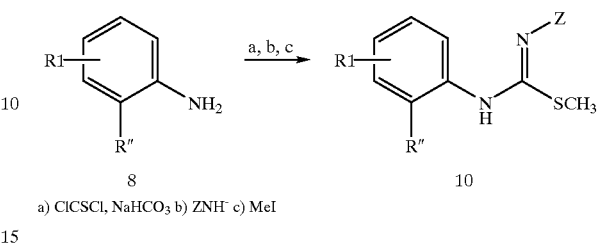

a) ClCSCl, NaHCO₃ b) ZNH⁻ c) MeI

The thioimidate (10, Scheme 5) can be converted to the title compound 4 by reaction with the amine R'NH₂. This reaction can be accelerated by the addition of metal salt with a high affinity for sulfur such as mercuric oxide or silver acetate or by oxidation of the sulfur with dimethyloxirane to form a better leaving group. Finally the phenol protection is removed by standard methods to form the title compound 4.

Scheme 5

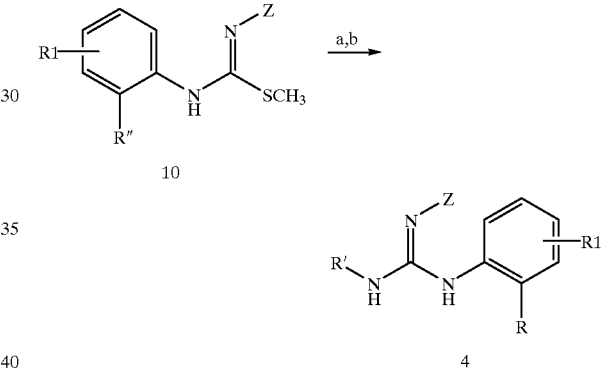

a) R'NH₂ b) deprotect

Alternately the title compound could be synthesized by reaction of a protected carbodiimide (11, Scheme 6) with the anion NH—Z (formed from reaction of NH₂Z with a base such as NaH) or the neutral species NH₂Z (Z=CN) and a tertiary amine base, such as Hünig's base (diisopropylethylamine), triethylamine, triisopropylethylamine, N,N-dimethylbenzylamine, or N,N-dimethylisopropylamine, under conditions where the nucleophile is present in large excess and the reaction time is kept as short as possible by carefully monitoring the reaction for completion followed by deprotection. Other suitable bases for use herein include, secondary amine, such as pyridine, and amino substituted pyridine derivatives. Suitable solvents for use herein when Z is cyano include various aprotic solvents, such as acetonitrile; halogenated solvents, such as chloroform and methylene chloride; ethyl gylcol-dimethyl ether (monoGLYME), dioxane, DMF and DMSO; or mixtures thereof, preferably acetonitrile. It is recognized by the skilled artisan that the limiting feature fo use of solvents herein will be the solubility of the cyano derivatived compound. For compounds wherein Z is other than cyano, while aprotic solvents are preferred, it is recognized by the skilled artisan that other suitable solvents, such as protic solvents, i.e. alcohols, may be used.

Preferably the reaction (when Z is cyano) temperature is from about −10° to about 100°, preferably about 10° to about 50°, more preferably around room temperature, i.e. 20 to 30° C.

The protected R″ moiety may be suitably deprotected using art recognized techniques. Preferably the deprotection is by deallylation catalyzed by palladium (O) when the protecting group is an allyl derivative.

Scheme 6

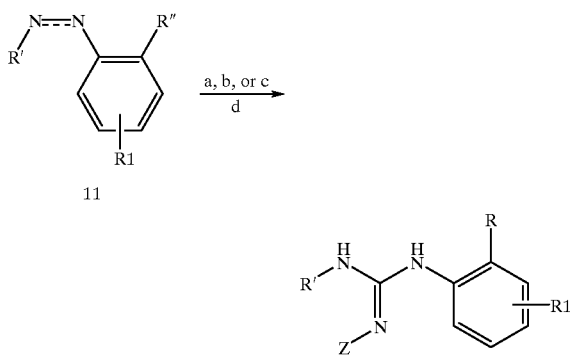

a) ZNH—(ZNH$^2$ + NaH) for Z = OR, COOEt, CHO, RNHSO$_2$, ArNHSO$_2$;
b) ZNH$_2$ HCl for Z = OH  c) ZNH2 and NR3 for Z = CN  d) deprotect The carbodiimide 11 is prepared from the thiourea (12a, Scheme 7) by treatment with phosgene and a tertiary amine base or from the thiourea (12a) or urea (12b) by reaction with triphenylphosphine, carbon tetrachloride and triethylamine.

The carbodiimide may also be prepared by reaction of the thiourea (12b) with an excess, such as 2 or more equivalents of methanesulfonyl chloride and a tertiary amine base, such as Hünig's base (diisopropylethylamine), triethylamine, triisopropylethylamine, N,N-dimethylbenzylamine, or N,N-dimethylisopropylamine, preferably triethylamine. The reaction may use any halogenated solvent, such as methylene chloride, chloroform, or tetrachloroethylene, etc.; suitable reaction temperatures are from about. −30° C. to about 80° C., preferably −10° C. to about 50° C., more preferably from about 0° C. to about room temperature. See Fell and Coppola (Fell, J. B., Coppola, J. B., Syn Communications 25, 43, (1995).

Scheme 7

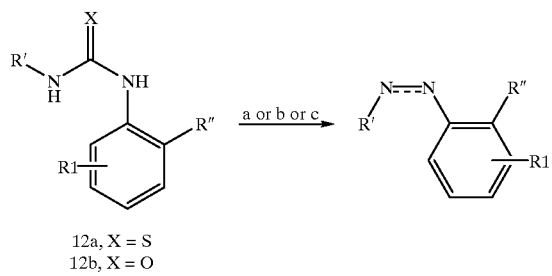

12a, X = S
12b, X = O a) phosgene, Et$_3$N, b) Ph$_3$P, CCl$_4$, Et$_3$N; c) MsCl, Et$_3$N The thiourea or urea derivative may be synthesized as described in the U.S. provisional application U.S. Ser. No. 60/020655 and WO96/25157, supra. The thiourea (12a, Scheme 8) may also be prepared by reaction of the protected ortho-substituted aniline and two equivalents of an appropriate base such as NaH, KH, calcium hydride, and reacting this anion with a commercially available isothiocyanate (W$_1$-NCS, wherein W$_1$ is as defined for compounds of Formula (I)). The reaction make take place in any suitable aprotic solvent or halogenated solvent, preferably dimethyl formamide. Suitable reaction temperatures for this reaction are from about −10° to about 50°.

If the desired isothiocyanate is not commercially available, it may be prepared by reaction of a corresponding aniline with thiophosgene and a suitable base such as sodium bicarbonate.

Scheme 8

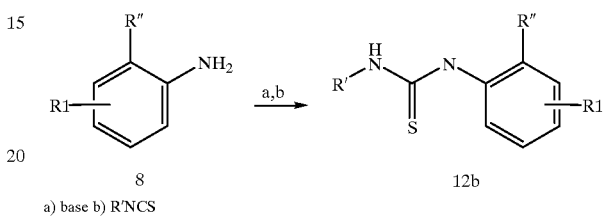

a) base  b) R'NCS

Another aspect of the present invention are the novel compounds of Formula (II)

$$W_1—N=C=N—HET \quad (II)$$

wherein W, and HET are as defined for formula (I), and W contains a protected or unprotected R group (R″) as defined for compounds of Formula (I).

Another aspect of the present invention are the novel compounds of Formula (III)

$$W_1—NH—C(S)—NH—HET \quad (III)$$

wherein W, and HET are as defined for formula (I), and W contains a protected or unprotected R group (R″) as defined for compounds of Formula (I).

Also, the protected (R″) versions of compounds of Formula (I) are contemplated as being within the scope of this invention.

It is recognized that the guanidine functionality may hve a number of different tautomers, such as W—N—C(=NZ)—N—HET; ZN=C(N—HET)—N—W; HET—N—C(=NW)—NZ, all of which are within the scope of this invention.

Pharmaceutically acceptable salts of compounds of Formula (I) may be obtained in known manner, for example by treatment thereof with an appropriate amount of acid or base in the presence of a suitable solvent.

Method of Treatment

The compounds of Formula (I), or a pharmaceutically acceptable salt thereof can be used in the manufacture of a medicament for the prophylactic or therapeutic treatment of any disease state in a human, or other mammal, which is exacerbated or caused by excessive or unregulated IL-8 cytokine production by such mammal's cell, such as but not limited to monocytes and/or macrophages, or other chemokines which bind to the IL-8 a or b receptor, also referred to as the type I or type II receptor.

Accordingly, the present invention provides a method of treating a chemokine mediated disease, wherein the chemokine is one which binds to an IL-8 a or b receptor and which method comprises administering an effective amount of a compound of Formula (I), or a pharmaceutically acceptable salt thereof. In particular, the chemokines are IL-8, GROα, GROβ, GROγ, ENA-78 or NAP-2.

The compounds of Formula (I) are administered in an amount sufficient to inhibit cytokine function, in particular IL-8, GROα, GROβ, GROγ, ENA-78 or NAP-2, such that they are biologically regulated down to normal levels of physiological function, or in some case to subnormal levels, so as to ameliorate the disease state. Abnormal levels of IL-8, GROα, GROβ, GROγ, ENA-78 or NAP-2 for instance in the context of the present invention, constitute: (i) levels of free IL-8 greater than or equal to 1 picogram per mL; (ii) any cell associated IL-8, GROα, GROβ, GROγ, ENA-78 or NAP-2 above normal physiological levels; or (iii) the presence of IL-8, GROα, GROβ, GROγ, ENA-78 or NAP-2 above basal levels in cells or tissues in which IL-8, GROα, GROβ, GROγ, ENA-78 or NAP-2 respectively, is produced.

There are many disease states in which excessive or unregulated IL-8 production is implicated in exacerbating and/or causing the disease. Chemokine mediated diseases include psoriasis, atopic dermatitis, arthritis, asthma, chronic obstructive pulmonary disease, adult respiratory distress syndrome, inflammatory bowel disease, Crohn's disease, ulcerative colitis, stroke, septic shock, endotoxic shock, gram negative sepsis, toxic shock syndrome, cardiac and renal reperfusion injury, glomerulonephritis, thrombosis, graft vs. host reaction, alzheimers disease, allograft rejections, malaria, restinosis, angiogenesis or undesired hematopoietic stem cells release.

These diseases are primarily characterized by massive neutrophil infiltration, T-cell infiltration, or neovascular growth, and are associated with increased IL-8, GROα, GROβ, GROγ or NAP-2 production which is responsible for the chemotaxis of neutrophils into the inflammatory site or the directional growth of endothelial cells. In contrast to other inflammatory cytokines (IL-1, TNF, and IL-6), IL-8, GROα, GROβ, GROγ or NAP-2 has the unique property of promoting neutrophil chemotaxis, enzyme release including but not limited to elastase release as well as superoxide production and activation. The α-chemokines but particularly, GROα, GROβ, GROγ or NAP-2, working through the IL-8 type I or II receptor can promote the neovascularization of tumors by promoting the directional growth of endothelial cells. Therefore, the inhibition of IL-8 induced chemotaxis or activation would lead to a direct reduction in the neutrophil infiltration.

Recent evidence also implicates the role of chemokines in the treatment of HIV infections, Littleman et al., Nature 381, pp661 (1996) and Koup et al., Nature 381, pp 667 (1996).

The present invention also provides for a means of treating, in an acute setting, as well as preventing, in those individuals deemed susceptible to, CNS injuries by the chemokine receptor antagonist compounds of Formula (I).

CNS injuries as defined herein include both open or penetrating head trauma, such as by surgery, or a closed head trauma injury, such as by an injury to the head region. Also included within this definition is ischemic stroke, particularly to the brain area.

Ischemic stroke may be defined as a focal neurologic disorder that results from insufficient blood supply to a particular brain area, usually as a consequence of an embolus, thrombi, or local atheromatous closure of the blood vessel. The role of inflammatory cytokines in this are has been emerging and the present invention provides a mean for the potential treatment of these injuries. Relatively little treatment, for an acute injury such as these has been available.

TNF-α is a cytokine with proinflammatory actions, including endothelial leukocyte adhesion molecule expression. Leukocytes infiltrate into ischemic brain lesions and hence compounds which inhibit or decrease levels of TNF would be useful for treatment of ischemic brain injury. See Liu et al., Stoke, Vol. 25., No. 7, pp 1481–88 (1994) whose disclosure is incorporated herein by reference.

Models of closed head injuries and treatment with mixed 5-LO/CO agents is discussed in Shohami et al., J. of Vaisc & Clinical Physiology and Pharmacology, Vol. 3, No. 2, pp. 99–107 (1992) whose disclosure is incorporated herein by reference. Treatment which reduced edema formation was found to improve functional outcome in those animals treated.

The compounds of Formula (I) are administered in an amount sufficient to inhibit IL-8, binding to the IL-8 alpha or beta receptors, from binding to these receptors, such as evidenced by a reduction in neutrophil chemotaxis and activation. The discovery that the compounds of Formula (I) are inhibitors of IL-8 binding is based upon the effects of the compounds of Formulas (I) in the in vitro receptor binding assays which are described herein. The compounds of Formula (I) have been shown, in some instances, to be dual inhibitors of both recombinant type I and type II IL-8 receptors. Preferably the compounds are inhibitors of only one receptor, more preferably Type II.

As used herein, the term "IL-8 mediated disease or disease state" refers to any and all disease states in which IL-8, GROα, GROβ, GROγ, ENA-78 or NAP-2 plays a role, either by production of IL-8, GROα, GROβ, GROγ or NAP-2 themselves, or by IL-8, GROα, GROβ, GROγ, ENA-78 or NAP-2 causing another monokine to be released, such as but not limited to IL-1, IL-6 or TNF. A disease state in which, for instance, IL-1 is a major component, and whose production or action, is exacerbated or secreted in response to IL-8, would therefore be considered a disease stated mediated by IL-8.

As used herein, the term "chemokine mediated disease or disease state" refers to any and all disease states in which a chemokine which binds to an IL-8 a or b receptor plays a role, such as but not limited to IL-8, GROα, GROβ, GROγ, ENA-78 or NAP-2. This would include a disease state in which, IL-8 plays a role, either by production of IL-8 itself, or by IL-8 causing another monokine to be released, such as but not limited to IL-1, IL-6 or TNF. A disease state in which, for instance, IL-1 is a major component, and whose production or action, is exacerbated or secreted in response to IL-8, would therefore be considered a disease stated mediated by IL-8.

As used herein, the term "cytokine" refers to any secreted polypeptide that affects the functions of cells and is a molecule which modulates interactions between cells in the immune, inflammatory or hematopoietic response. A cytokine includes, but is not limited to, inonokines and lymphokines, regardless of which cells produce them. For instance, a monokine is generally referred to as being produced and secreted by a mononuclear cell, such as a macrophage and/or monocyte. Many other cells however also produce monokines, such as natural killer cells, fibroblasts, basophils, neutrophils, endothelial cells, brain astrocytes, bone marrow stromal cells, epideral keratinocytes and B-lymphocytes. Lymphokines are generally referred to as being produced by lymphocyte cells. Examples of cytokines include, but are not limited to, Interleukin-1 (IL-1), Interleukin-6 (IL-6), Interleukin-8 (IL-8), Tumor Necrosis Factor-alpha (TNF-α) and Tumor Necrosis Factor beta (TNF-β).

As used herein, the term "chemokine" refers to any secreted polypeptide that affects the functions of cells and is a molecule which modulates interactions between cells in the immune, inflammatory or hematopoietic response, similar to the term "cytokine" above. A chemokine is primarily secreted through cell transmembranes and causes chemotaxis and activation of specific white blood cells and leukocytes, neutrophils, monocytes, macrophages, T-cells, B-cells, endothelial cells and smooth muscle cells. Examples of chemokines include, but are not limited to, IL-8, GRO-α, GRO-β, GROγ, ENA-78, NAP-2, IP-10, MIP-1α, MIP-β, PF4, and MCP 1, 2, and 3.

In order to use a compound of Formula (I) or a pharmaceutically acceptable salt thereof in therapy, it will normally be formulated into a pharmaceutical composition in accordance with standard pharmaceutical practice. This invention, therefore, also relates to a pharmaceutical composition comprising an effective, non-toxic amount of a compound of Formula (I) and a pharmaceutically acceptable carrier or diluent.

Compounds of Formula (I), pharmaceutically acceptable salts thereof and pharmaceutical compositions incorporating such may conveniently be administered by any of the routes conventionally used for drug administration, for instance, orally, topically, parenterally or by inhalation. The compounds of Formula (I) may be administered in conventional dosage forms prepared by combining a compound of Formula (I) with standard pharmaceutical carriers according to conventional procedures. The compounds of Formula (I) may also be administered in conventional dosages in combination with a known, second therapeutically active compound. These procedures may involve mixing, granulating and compressing or dissolving the ingredients as appropriate to the desired preparation. It will be appreciated that the form and character of the pharmaceutically acceptable character or diluent is dictated by the amount of active ingredient with which it is to be combined, the route of administration and other well-known variables. The carrier(s) must be "acceptable" in the sense of being compatible with the other ingredients of the formulation and not deleterious to the recipient thereof.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time delay material well known to the art, such as glyceryl mono-stearate or glyceryl distearate alone or with a wax.

A wide variety of pharmaceutical forms can be employed. Thus, if a solid carrier is used, the preparation can be tableted, placed in a hard gelatin capsule in powder or pellet form or in the form of a troche or lozenge. The amount of solid carrier will vary widely but preferably will be from about 25 mg. to about 1 g. When a liquid carrier is used, the preparation will be in the form of a syrup, emulsion, soft gelatin capsule, sterile injectable liquid such as an ampule or nonaqueous liquid suspension.

Compounds of Formula (I) may be administered topically, that is by non-systemic administration. This includes the application of a compound of Formula (I) externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as liniments, lotions, creams, ointments or pastes, and drops suitable for administration to the eye, ear or nose. The active ingredient may comprise, for topical administration, from 0.001% to 10% w/w, for instance from 1% to 2% by weight of the Formulation. It may however comprise as much as 10% w/w but preferably will comprise less than 5% w/w, more preferably from 0.1% to 1% w/w of the Formulation.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy base. The base may comprise hydrocarbons such as hard, soft or liquid paraffin, glycerol, beeswax, a metallic soap; a mucilage; an oil of natural origin such as almond, corn, arachis, castor or olive oil; wool fat or its derivatives or a fatty acid such as steric or oleic acid together with an alcohol such as propylene glycol or a macrogel. The formulation may incorporate any suitable surface active agent such as an anionic, cationic or non-ionic surfactant such as a sorbitan ester or a polyoxyethylene derivative thereof. Suspending agents such as natural gums, cellulose derivatives or inorganic materials such as silicaceous silicas, and other ingredients such as lanolin, may also be included.

Drops according to the present invention may comprise sterile aqueous or oily solutions or suspensions and may be prepared by dissolving the active ingredient in a suitable aqueous solution of a bactericidal and/or fungicidal agent and/or any other suitable preservative, and preferably including a surface active agent. The resulting solution may then be clarified by filtration, transferred to a suitable container which is then sealed and sterilized by autoclaving or maintaining at 98–100° C. for half an hour. Alternatively, the solution may be sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Compounds of formula (I) may be administered parenterally, that is by intravenous, intramuscular, subcutaneous intranasal, intrarectal, intravaginal or intraperitoneal administration. The subcutaneous and intramuscular forms of parenteral administration are generally preferred. Appropriate dosage forms for such administration may be prepared by conventional techniques. Compounds of Formula (I) may also be administered by inhalation, that is by intranasal and oral inhalation administration. Appropriate dosage forms for such administration, such as an aerosol formulation or a metered dose inhaler, may be prepared by conventional techniques.

For all methods of use disclosed herein for the compounds of Formula (I), the daily oral dosage regimen will preferably be from about 0.01 to about 80 mg/kg of total body weight. The daily parenteral dosage regimen about 0.001 to about 80 mg/kg of total body weight. The daily topical dosage regimen will preferably be from 0.1 mg to 150 mg, administered one to four, preferably two or three times daily. The daily inhalation dosage regimen will preferably be from about 0.01 mg/kg to about 1 mg/kg per day. It will also be recognized by one of skill in the art that the optimal quantity and spacing of individual dosages of a compound of Formula (I) or a pharmaceutically acceptable salt thereof will be determined by the nature and extent of the condition being treated, the form, route and site of administration, and the particular patient being treated, and that such optimums can be determined by conventional techniques. It will also be appreciated by one of skill in the art that the optimal course of treatment, i.e., the number of doses of a compound of Formula (I) or a pharmaceutically acceptable salt thereof given per day for a defined number of days, can be ascertained by those skilled in the art using conventional course of treatment determination tests.

The invention will now be described by reference to the following biological examples which are merely illustrative and are not to be construed as a limitation of the scope of the present invention.

BIOLOGICAL EXAMPLES

The IL-8, and Gro-α chemokine inhibitiory effects of compounds of the present invention were determined by the following in vitro assay:

Receptor Binding Assays

[125I] IL-8 (human recombinant) is obtained from Amersham Corp., Arlington Heights, Ill., with specific activity 2000 Ci/mmol. Gro-α is obtained from NEN-New England Nuclear. All other chemicals are of analytical grade. High levels of recombinant human IL-8 type α and β receptors were individually expressed in Chinese hamster ovary cells as described previously (Holmes, et al., *Science*, 1991, 253, 1278). The Chinese hamster ovary membranes were homogenized according to a previously described protocol (Haour, et al., *J Biol Chem.*, 249 pp 2195–2205 (1974)). Except that the homogenization buffer is changed to 10 mM Tris-HCL, 1 mM MgSO4, 0.5 mM EDTA (ethylene-diaminetetra-acetic acid), 1 mMPMSF (α-toluenesulphonyl fluoride), 0.5 mg/L Leupeptin, pH 7.5. Membrane protein concentration is determined using Pierce Co. micro-assay kit using bovine serum albumin as a standard. All assays are performed in a 96-well micro plate format. Each reaction mixture contains $^{125}$I IL-8 (0.25 nM) or $^{125}$I Gro-α and 0.5 µg/mL of IL-8Rα or 1.0 µg/mL of IL-8Rβ membranes in 20 mM Bis-Trispropane and 0.4 mM Tris HCl buffers, pH 8.0, containing 1.2 mM MgSO$_4$, 0.1 mM EDTA, 25 mM NaCl and 0.03% CHAPS. In addition, drug or compound of interest ss added which has been pre-dissolved in DMSO so as to reach a final concentration of between 0.01 nM and 100 uM. The assay is initiated by addition of $^{125}$I-IL-8. After 1 hour at room temperature the plate is harvested using a Tomtec 96-well harvester onto a glass fiber filtermat blocked with 1% polyethylenimine/0.5% BSA and washed 3 times with 25 mM NaCl, 10 mM TrisHCl, 1 mM MgSO$_4$, 0.5 mM EDTA, 0.03% CHAPS, pH 7.4. The filter is then dried and counted on the Betaplate liquid scintillation counter. The recombinant IL-8 Rα, or Type I, receptor is also referred to herein as the non-permissive receptor and the recombinant IL-8 Rβ, or Type II, receptor is referred to as the permissive receptor.

Chemotaxis Assay

The in vitro inhibitory properties of these compounds are determined in the neutrophil chemotaxis assay as described in Current Protocols in Immunology, vol I, Suppl 1, Unit 6.12.3., whose disclosure is incorporated herein by reference in its entirety. Neutrophils where isolated from human blood as described in Current Protocols in Immunology Vol I, Suppl 1 Unit 7.23.1, whose disclosure is incorporated herein by reference in its entirety. The chemoattractants IL-8, GRO-α, GRO-β, GRO-γ and NAP-2 are placed in the bottom chamber of a 48 multiwell chamber (Neuro Probe, Cabin John, MD) at a concentration between 0.1 and 100 nM. The two chambers are separated by a 5 um polycarbonate filter. When compounds of this invention are tested, they are mixed with the cells (0.001–1000 nM) just prior to the addition of the cells to the upper chamber. Incubation is allowed to proceed for between about 45 and 90 min at about 37° C. in a humidified incubator with 5% $CO_2$. At the end of the incubation period, the polycarbonate membrane is removed and the top side washed, the membrane then stained using the Diff Quick staining protocol (Baxter Products, McGaw Park, Ill., USA). Cells which have chemotaxed to the chemokine are visually counted using a microscope. Generally, four fields are counted for each sample, these numbers are averaged to give the average number of cells which had migrated. Each sample is tested in triplicate and each compound repeated at least four times. To certain cells (positive control cells) no compound is added, these cells represent the maximum chemotactic response of the cells. In the case where a negative control (unstimulated) is desired, no chemokine is added to the bottom chamber. The difference between the positive control and the negative control represents the chemotactic activity of the cells.

Elastase Release Assay

The compounds of this invention are tested for their ability to prevent Elastase release from human neutrophils. Neutrophils are isolated from human blood as described in Current Protocols in Immunology Vol I, Suppl I Unit 7.23.1. PMNs 0.88×10$^6$ cells suspended in Ringer's Solution (NaCl 118, KCl 4.56, NaHCO3 25, KH2PO4 1.03, Glucose 11.1, HEPES 5 mM, pH 7.4) are placed in each well of a 96 well plate in a volume of 50 ul. To this plate is added the test compound (0.001–1000 nM) in a volume of 50 ul, Cytochalasin B in a volume of 50 ul (20 ug/ml) and Ringers buffer in a volume of 50 ul. These cells are allowed to warm (37° C., 5% CO2, 95% RH) for 5 min before IL-8, GROα, GROβ, GROγ or NAP-2 at a final concentration of 0.01–1000 nM was added. The reaction is allowed to proceed for 45 min before the 96 well plate is centrifuged (800×g 5 min) and 100 ul of the supernatant removed. This suppernatant is added to a second 96 well plate followed by an artificial elastase substrate (MeOSuc-Ala-Ala-Pro-Val-AMC, Nova Biochem, La Jolla, Calif.) to a final concentration of 6 ug/mL dissolved in phosphate buffered saline. Immediately, the plate is placed in a fluorescent 96 well plate reader (Cytofluor 2350, Millipore, Bedford, Mass.) and data collected at 3 min intervals according to the method of Nakajima et al J. Biol Chem 254 4027 (1979). The amount of Elastase released from the PMNs is calculated by measuring the rate of MeOSuc-Ala-Ala-Pro-Val-AMC degradation.

TNF-α in Traumatic Brain Injury Assay

The present assay provides for examination of the expression of tumor necrosis factor mRNA in specfic brain regions which follow experimentally induced lateral fluid-percussion traumatic brain injury (TBI) in rats. Adult Sprague-Dawley rats (n=42) were anesthetized with sodium pentobarbital (60 mg/kg, i.p.) and subjected to lateral fluid-percussion brain injury of moderate severity (2.4 atm.) centered over the left temporaparietal cortex (n=18), or "sham" treatment (anesthesia and surgery without injury, n=18). Animals are sacrificed by decapitation at 1, 6 and 24 hr. post injury, brains removed, and tissue samples of left (injured) parietal cortex (LC), corresponding area in the contralateral right cortex (RC), cortex adjacent to injured parietal cortex (LA), corresponding adjacent area in the right cortex (RA), left hippocampus (LH) and right hippocampus (RH) are prepared. Total RNA was isolated and Northern blot hybridization is performed and quantitated relative to an TNF-α positive control RNA (macrophage=100%). A marked increase of TNF-α mRNA expression is observed in LH (104±17% of positive control, p<0.05 compared with sham), LC (105±21%, p<0.05) and LA (69±8%, p<0.01) in the traumatized hemisphere 1 hr. following injury. An increased TNF-α mRNA expression is also observed in LH (46±8%, p<0.05), LC (30±3%, p<0.01) and LA (32±3%, p<0.01) at 6 hr. which resolves by 24 hr. following injury. In the contralateral hemisphere, expression of TNF-α mRNA is increased in RH (46±2%, p<0.01), RC (4±3%) and RA (22±8%) at 1 hr. and in RH (28±11%), RC (7±5%) and RA (26±6%, p<0.05) at 6 hr. but not at 24 hr. following injury. In sham (surgery without injury) or naive animals, no consistent changes in expression of TNF-α mRNA are observed in any of the 6 brain areas in either hemisphere at any times. These results indicate that following parasagittal fluid-percussion brain injury, the temporal expression of TNF-α mRNA is altered in specific brain regions, including those of the non-traumatized hemisphere. Since TNF-α is able to induce nerve growth factor (NGF) and stimulate the release of other cytokines from activated astrocytes, this post-traumatic alteration in gene expression of TNF-α plays an important role in both the acute and regenerative response to CNS trauma.

CNS Injury model for IL-β mRNA

This assay characterizes the regional expression of interleukin-1β (IL-1β) mRNA in specific brain regions following experimental lateral fluid-percussion traumatic brain injury (TBI) in rats. Adult Sprague-Dawley rats (n=42) are anesthetized with sodium pentobarbital (60 mg/kg, i.p.) and subjected to lateral fluid-percussion brain injury of moderate severity (2.4 atm.) centered over the left temporaparietal cortex (n=18), or "sham" treatment (anesthesia and surgery without injury). Animals are sacrificed at 1, 6 and 24 hr. post injury, brains removed, and tissue samples of left (injured) parietal cortex (LC), corresponding area in the contralateral right cortex (RC), cortex adjacent to injured parietal cortex (LA), corresponding adjacent area in the right cortex (RA), left hippocampus (LH) and right hippocampus (RH) are prepared. Total RNA is isolated and Northern blot hybridization was performed and the quantity of brain tissue IL-1β mRNA is presented as percent relative radioactivity of IL-1β positive macrophage RNA which was loaded on same gel. At 1 hr. following brain injury, a marked and significant increase in expression of IL-1β mRNA is observed in LC (20.0±0.7% of positive control, n=6, p<0.05 compared with sham animal), LH (24.5±0.9%, p<0.05) and LA (21.5±3.1%, p<0.05) in the injured hemisphere, which remained elevated up to 6 hr. post injury in the LC (4.0±0.4%, n=6, p<0.05) and LH (5.0±1.3%, p<0.05). In sham or naive animals no expression of IL-1β mRNA is observed in any of the respective brain areas. These results indicate that following TBI, the temporal expression of IL-1β mRNA is regionally stimulated in specific brain regions. These regional changes in cytokines, such as IL-1β play a role in the post-traumatic.

All publications, including but not limited to patents and patent applications, cited in this specification are herein incorporated by reference as if each individual publication were specifically and individually indicated to be incorporated by reference herein as though fully set forth.

The above description fully discloses the invention including preferred embodiments thereof. Modifications and improvements of the embodiments specifically disclosed herein are within the scope of the following claims. Without further elaboration, it is believed that one skilled in the are can, using the preceding description, utilize the present invention to its fullest extent. Therefore the Examples herein are to be construed as merely illustrative and not a limitation of the scope of the present invention in any way. The embodiments of the invention in which an exclusive property or privilege is claimed are defined as follows.

What is claimed is:

1. A method of treating a chemokine mediated disease state, wherein the chemokine binds to an IL-8 α or β receptor in a mammal, which comprises administering to said mammal an effective amount of a compound of the formula:

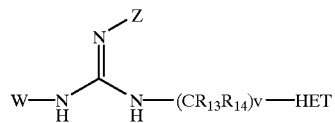

(I)

wherein

Z is cyano;

R is OH;

$R_1$ is independently selected from hydrogen; halogen; nitro; cyano; halosubstituted $C_{1-10}$ alkyl; $C_{1-10}$ alkyl; $C_{2-10}$ alkenyl; $C_{1-10}$ alkoxy; halosubstituled $C_{1-10}$ alkoxy; azide; $(CR_8R_8)q$ $S(O)_tR_4$; hydroxy; hydroxy $C_{1-4}$alkyl; aryl; aryl $C_{1-4}$ alkyl; aryloxy; aryl $C_{1-4}$ alkyloxy; aryl $C_{2-10}$ alkenyl; $(CR_8R_8)qNR_4R_5$; $C_{2-10}$ alkenyl $C(O)NR_4R_5$; $(CR_8R_8)q$ $C(O)NR_4R_5$; $(CR_8R_8)q$ $C(O)NR_4R_{10}$; $S(O)_3H$; $S(O)_3R_8$; $(CR_8R_8)q$ $C(O)R_{11}$; $C_{2-10}$ alkenyl $C(O)R_{11}$; $C_{2-10}$ alkenyl $C(O)OR_{11}$; $(CR_8R_8)q$ $C(O)OR_{12}$; $(CR_8R_8)q$ $OC(O)R_{11}$; $(CR_8R_8)qNR_4C(O)R_{11}$; $(CR_8R_8)q$ $NHS(O)_2R_{19}$; $(CR_8R_8)q$ $S(O)_2NR_4R_5$; or a 5 to 6 membered saturated or unsaturated ring, and wherein the aryl moiety may be optionally substituted;

m is an integer having a value of 1 to 3;

q is 0, or an integer having a value of 1 to 10;

s is an integer having a value of 1 to 3;

t is 0, or an integer having a value of 1 or 2;

v is 0, or an integer having a value of 1 to 4;

$R_4$ and $R_5$ are independently hydrogen, optionally substituted $C_{1-4}$ alkyl, optionally substituted aryl, or optionally substituted aryl $C_{1-4}$alkyl;

HET is a six-membered ring with one nitrogen atom;

$R_6$ and $R_7$ are independently hydrogen or a $C_{1-4}$ alkyl group;

$R_8$ is independently selected from hydrogen or $C_{1-4}$ alkyl;

$R_{10}$ is $C_{1-10}$ alkyl $C(O)_2R_8$;

$R_{11}$ is hydrogen, $C_{1-4}$ alkyl, optionally substituted aryl, or optionally substituted aryl $C_{1-4}$alkyl;

$R_{12}$ is hydrogen, $C_{1-10}$ alkyl, optionally substituted aryl or optionally substituted arylalkyl;

$R_{13}$ and $R_{14}$ are independently hydrogen or $C_{1-4}$ alkyl;

$R_{15}$ and $R_{16}$ are independently hydrogen, optionally substituted $C_{1-4}$ alkyl, optionally substituted aryl, or optionally substituted aryl $C_{1-4}$alkyl;

$R_{17}$ is $C_{1-4}$ alkyl, $NR_{15}R_{16}$, $OR_{11}$, optionally substituted aryl, or optionally substituted aryl $C_{1-4}$alkyl;

$R_{18}$ is optionally substituted $C_{1-4}$ alkyl, optionally substituted aryl, or optionally substituted aryl $C_{1-4}$alkyl;

$R_{19}$ is $C_{1-4}$alkyl, aryl, or aiylalkyl, wherein the all of these moieties may be optionally substituted;

$R_d$ is $NR_6R_7$, alkyl, aryl$C_{1-4}$ alkyl, aryl$C_{2-4}$ alkenyl, wherein the alkyl, or aryl containing moieities may be optionally substituted;

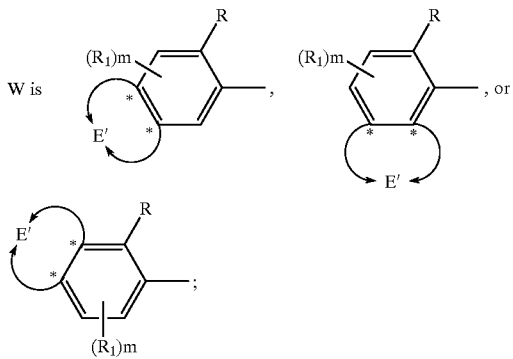

the E' containing ring is optionally selected from

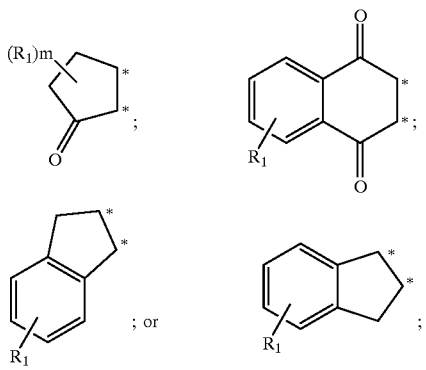

the asterix * denoting point of attachment of the ring; or a pharmaceutically acceptable salt thereof.

2. The method according to claim 1 wherein the $R_2$ is optionally substituted one to three times by halogen, nitro, halosubstituted $C_{1-10}$ alkyl, $C_{1-10}$ alkyl, $C_{1-10}$ alkoxy, OH, SH, $C(O)NR_6R_7$, NH—$C(O)R_a$, $NHS(O)R_b$, $S(O)NR_6R_7$, or $C(O)OR_8$.

3. The method according to claim 1 wherein $R_1$ is halogen, cyano, nitro, $CF_3$, $C(O)NR_4R_5$, alkenyl $C(O)NR_4R_5$, $C(O)R_4R_{10}$, alkenyl $C(O)OR_{12}$, or $S(O)NR_4R_5$.

4. The method according to claim 1 wherein HET is substituted by $(Y)_n$;

n is an integer having a value of 1 to 3;

Y is independently selected from hydrogen; halogen; nitro, cyano; halosubstituted $C_{1-10}$ alkyl; $C_{1-10}$ alkyl; $C_{2-10}$ alkenyl; $C_{1-10}$ alkoxy; halosubstituted $C_{1-10}$ alkoxy; azide; $(CR_8R_8)q$ $S(O)_rR_4$; hydroxy; hydroxy$C_{1-4}$alkyl; aryl; aryl $C_{1-4}$ alkyl; aryloxy; aryl$C_{1-4}$ alkyloxy; aryl $C_{2-10}$ alkenyl; $(CR_8R_8)q$ $NR_4R_5$; $C_{2-10}$ alkenyl $C(O)NR_4R_5$; $(CR_8R_8)q$ $C(O)NR_4R_5$; $(CR_8R_8)q$ $C(O)NR_4R_{10}$; $S(O)_3H$; $S(O)_3R_8$; $(CR_8R_8)q$ $C(O)R_{11}$; $C_{2-10}$ alkenyl $C(O)R_{11}$; $C_{2-10}$ alkenyl $C(O)OR_{11}$; $(CR_8R_8)q$ $C(O)OR_{12}$; $(CR_8R_8)q$ $OC(O)R_{11}$; $(CR_8R_8)q$ $NR_4C(O)R_{11}$; $(CR_8R_8)q$ $NHS(O)_2R_d$; or $(CR_8R_8)q$ $S(O)_2NR_4R_5$ or a 5 to 6 membered saturated or unsaturated ring; wherein the aryl containing moieties may be optionally substituted as defined herein; and $R_d$ is $NR_6R_7$, alkyl, aryl$C_{1-4}$ alkyl, aryl$C_{2-4}$ alkenyl, wherein the alkyl, or the aryl containing moieties may be optionally substituted.

5. The method according to claim 4 wherein Y is halogen, $C_{1-4}$ alkoxy, optionally substituted aryl, optionally substituted arylalkoxy, methylene dioxy, $NR_4R_5$, thio$C_{1-4}$alkyl, thioaryl, halosubstituted alkoxy, optionally substituted $C_{1-4}$alkyl, or hydroxy alkyl.

6. The method according to claim 1 wherein the mammal is afflicted with a chemokine mediated disease selected from psoriasis, atopic dermatitis, asthma, chronic obstructive pulmonary disease, adult respiratory distress syndrome, arthritis, inflammatory bowel disease, Crohn's disease, ulcerative colitis, septic shock, endotoxic shock, gram negative sepsis, toxic shock syndrome, stroke, cardiac and renal reperfusion injury, glomerulo-nephritis, thrombosis, alzheimers disease, graft vs. host reaction, or allograft rejections.

* * * * *